US011433244B2

(12) United States Patent
Chu (10) Patent No.: US 11,433,244 B2
(45) Date of Patent: Sep. 6, 2022

(54) CARDIAC PACING DEVICE AND SYSTEM

(71) Applicant: Chang Gung Memorial Hospital, Linkou, Taoyuan (TW)

(72) Inventor: Pao-Hsien Chu, Taoyuan (TW)

(73) Assignee: Chang Gung Memorial Hospital, Linkou, Taoyuan (TW)

( * ) Notice: Subject to any disclaimer, the term of this patent is extended or adjusted under 35 U.S.C. 154(b) by 3 days.

(21) Appl. No.: 16/359,774

(22) Filed: Mar. 20, 2019

(65) Prior Publication Data

US 2019/0299011 A1 Oct. 3, 2019

(30) Foreign Application Priority Data

Mar. 31, 2018 (TW) .................. 107111438
Sep. 13, 2018 (TW) .................. 107132242

(51) Int. Cl.
| | | |
|---|---|---|
| *A61N 1/37* | (2006.01) | |
| *A61N 1/375* | (2006.01) | |
| *A61N 1/368* | (2006.01) | |
| *A61B 17/12* | (2006.01) | |
| *A61B 5/00* | (2006.01) | |
| *A61N 1/372* | (2006.01) | |
| *A61B 5/024* | (2006.01) | |
| *A61B 5/363* | (2021.01) | |

(Continued)

(52) U.S. Cl.
CPC ............ *A61N 1/3718* (2013.01); *A61B 5/024* (2013.01); *A61B 5/363* (2021.01); *A61B 5/686* (2013.01); *A61B 5/6869* (2013.01); *A61B 17/12122* (2013.01); *A61B 17/12172* (2013.01); *A61B 17/12177* (2013.01); *A61N 1/3688* (2013.01); *A61N 1/3756* (2013.01); *A61N 1/37205* (2013.01); *A61N 1/37512* (2017.08); *A61N 1/368* (2013.01); *A61N 1/3627* (2013.01); *A61N 1/36592* (2013.01); *A61N 1/37211* (2013.01); *A61N 1/37518* (2017.08)

(58) Field of Classification Search
CPC ....... A61B 5/024; A61B 5/0464; A61B 5/686; A61B 5/6869; A61B 17/12122; A61B 17/12172; A61B 17/12177; A61N 1/3718; A61N 1/37512; A61N 1/3688; A61N 1/37205; A61N 1/3756; A61N 1/37518; A61N 1/3627; A61N 1/36592; A61N 1/368; A61N 1/37211
USPC .......................................................... 607/9
See application file for complete search history.

(56) References Cited

U.S. PATENT DOCUMENTS

| | | | | |
|---|---|---|---|---|
| 2009/0234407 | A1* | 9/2009 | Hastings | ............ A61N 1/36842 607/14 |
| 2011/0276075 | A1* | 11/2011 | Fung | .................. A61B 18/1815 606/185 |

(Continued)

*Primary Examiner* — Carl H Layno
*Assistant Examiner* — Michael J Lau
(74) *Attorney, Agent, or Firm* — Reinhart Boerner Van Deuren P.C.

(57) ABSTRACT

A cardiac pacing device to be disposed in a heart between an atrium and an atrial appendage protruding from the atrium includes a blocker and a regulator attached to the blocker. The blocker is configured to occlude the atrial appendage. The regulator is configured to contact the heart when the blocker is positioned between the atrium and the atrial appendage to occlude the atrial appendage in order to regulate a cardiac rhythm of the heart accordingly.

8 Claims, 9 Drawing Sheets

(51) Int. Cl.
    *A61N 1/365*     (2006.01)
    *A61N 1/362*     (2006.01)

(56) References Cited

U.S. PATENT DOCUMENTS

| | | | |
|---|---|---|---|
| 2012/0283585 A1* | 11/2012 | Werneth | A61B 17/0057 600/508 |
| 2013/0018413 A1* | 1/2013 | Oral | A61B 17/0057 606/213 |
| 2013/0150912 A1* | 6/2013 | Perschbacher | A61N 1/36585 607/18 |
| 2014/0039536 A1* | 2/2014 | Cully | A61B 17/12136 606/194 |
| 2014/0188157 A1* | 7/2014 | Clark | A61B 17/12122 606/200 |
| 2015/0196756 A1* | 7/2015 | Stahmann | A61N 1/37288 607/4 |
| 2017/0281193 A1* | 10/2017 | Asirvatham | A61B 17/12177 |
| 2017/0340336 A1* | 11/2017 | Osypka | B33Y 10/00 |
| 2018/0078218 A1* | 3/2018 | Moisa | A61B 5/748 |
| 2020/0107836 A1* | 4/2020 | O'Halloran | A61B 17/12136 |
| 2020/0253615 A1* | 8/2020 | Melanson | A61N 1/37205 |

* cited by examiner

CARDIAC PACING DEVICE AND SYSTEM

CROSS-REFERENCE TO RELATED APPLICATION

This application claims priority of Taiwanese Invention Patent Application No. 107111438, filed on Mar. 31, 2018, and Taiwanese Invention Patent Application No. 107132242, filed on Sep. 13, 2018.

FIELD

The disclosure relates to a cardiac pacing system including a cardiac pacing device to be disposed in a heart between an atrium and an atrial appendage protruding from the atrium.

BACKGROUND

A normal heart rate for human is about 70 beats per minute (bpm). However, the heart rate may slow down due to aging, endocrine disorders, coronary heart disease (CAD), etc. In a severe case, the heart rate may be lower than 40 bpm or a cardiac pause lasting 3-6 seconds may occur, which may lead to symptoms of dizziness, tachypnea, fatigue, pedal edema, or even syncope, since the blood cannot bring enough oxygen to every part of the human body. For a patient with such heart disease, his/her doctor may advise the patient to implant a cardiac pacing device (i.e., an artificial pacemaker) to maintain adequate cardiac rhythm.

A conventional artificial pacemaker is composed of three parts which are a pulse generator, an electrode and a lead. The pulse generator is a metal box with a battery and an electrical circuit inside, and is connected to the electrode via the lead. The operation of implanting the artificial pacemaker includes implanting the pulse generator under the clavicle of the patient, and pushing the electrode with the lead into an atrium or a ventricle of the heart through the venous system, such that the pulse generator may timely deliver an electrical impulse to the heart muscles via the electrode for regulating the cardiac rhythm when detecting bradycardia.

SUMMARY

An object of the disclosure is to provide improved cardiac pacing devices and systems that are more convenient to implant and/or use than the prior art, and that may provide more functions than the conventional artificial pacemaker.

According to one aspect of the disclosure, a cardiac pacing device is to be disposed in a heart between an atrium and an atrial appendage protruding from the atrium. The cardiac pacing device includes a blocker configured to occlude the atrial appendage. The cardiac pacing device further includes a regulator attached to the blocker. The regulator is configured to contact the heart when the blocker is positioned between the atrium and the atrial appendage to occlude the atrial appendage in order to regulate cardiac rhythm of the heart.

According to one aspect of the disclosure, a cardiac pacing system for regulating cardiac rhythm of a heart includes a first cardiac pacing device to be disposed in the heart between a left atrium and a left atrial appendage protruding from the left atrium, a second cardiac pacing device to be positioned in a right ventricle of the heart, and a control device capable of communicating with the first and second cardiac pacing devices. The first cardiac pacing device includes a blocker and a regulator attached to the blocker. The blocker is configured to occlude the left atrial appendage. The regulator is configured to contact the heart when the blocker is positioned between the left atrium and the left atrial appendage to occlude the left atrial appendage in order to sense a heart rate of the heart and to regulate the cardiac rhythm of the heart. The second cardiac pacing device is configured to sense the heart rate of the heart and to regulate the cardiac rhythm of the heart. The control device is configured to trigger at least one of the first cardiac pacing device or the second cardiac pacing device to stimulate at least one of the left atrium or the right ventricle based on the heart rate sensed by the at least one of the first cardiac pacing device or the second cardiac pacing device.

According to one aspect of the disclosure, a cardiac pacing system for regulating cardiac rhythm of a heart includes a first cardiac pacing device to be disposed in the heart between a right atrium and a right atrial appendage protruding from the right atrium, a second cardiac pacing device to be positioned in a right ventricle of the heart, and a control device capable of communicating with the first and second cardiac pacing devices. The first cardiac pacing device includes a blocker and a regulator attached to the blocker. The blocker is configured to occlude the right atrial appendage. The regulator is configured to contact the heart when the blocker is positioned between the right atrium and the right atrial appendage to occlude the right atrial appendage in order to sense a heart rate of the heart and to regulate the cardiac rhythm of the heart. The second cardiac pacing device is configured to sense the heart rate of the heart and to regulate the cardiac rhythm of the heart. The control device is configured to trigger at least one of the first cardiac pacing device or the second cardiac pacing device to stimulate at least one of the right atrium or the right ventricle based on the heart rate sensed by the at least one of the first cardiac pacing device or the second cardiac pacing device.

BRIEF DESCRIPTION OF THE DRAWINGS

Other features and advantages of the disclosure will become apparent in the following detailed description of the embodiment(s) with reference to the accompanying drawings, of which.

DETAILED DESCRIPTION

Before the disclosure is described in greater detail, it should be noted that where considered appropriate, reference numerals or terminal portions of reference numerals have been repeated among the figures to indicate corresponding or analogous elements, which may optionally have similar characteristics.

Figure 1:
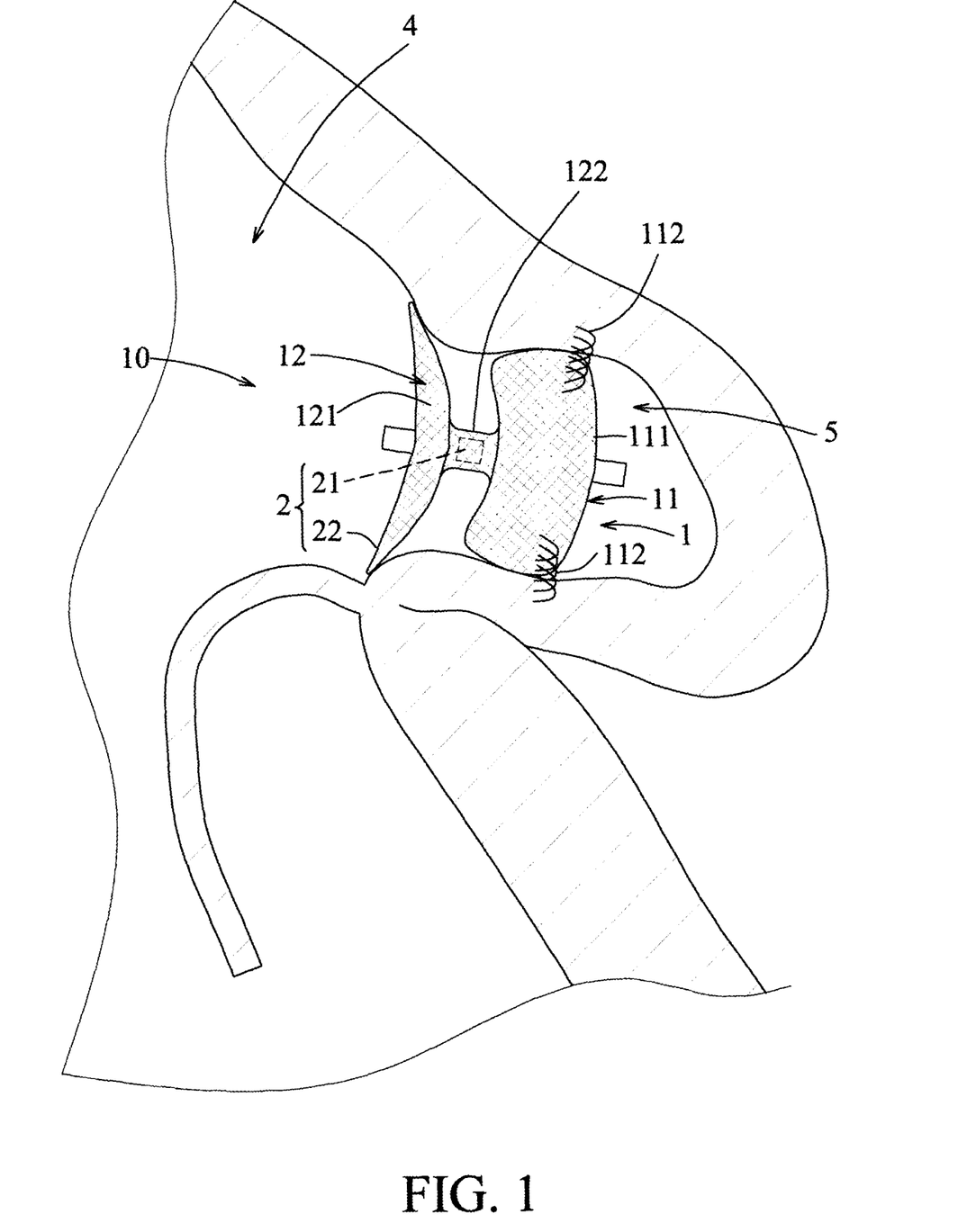
FIG. 1 is a schematic view exemplarily illustrating an example of a cardiac pacing device disposed in a heart between the left atrium and the left atrial appendage, according to an embodiment.
Figure 2:
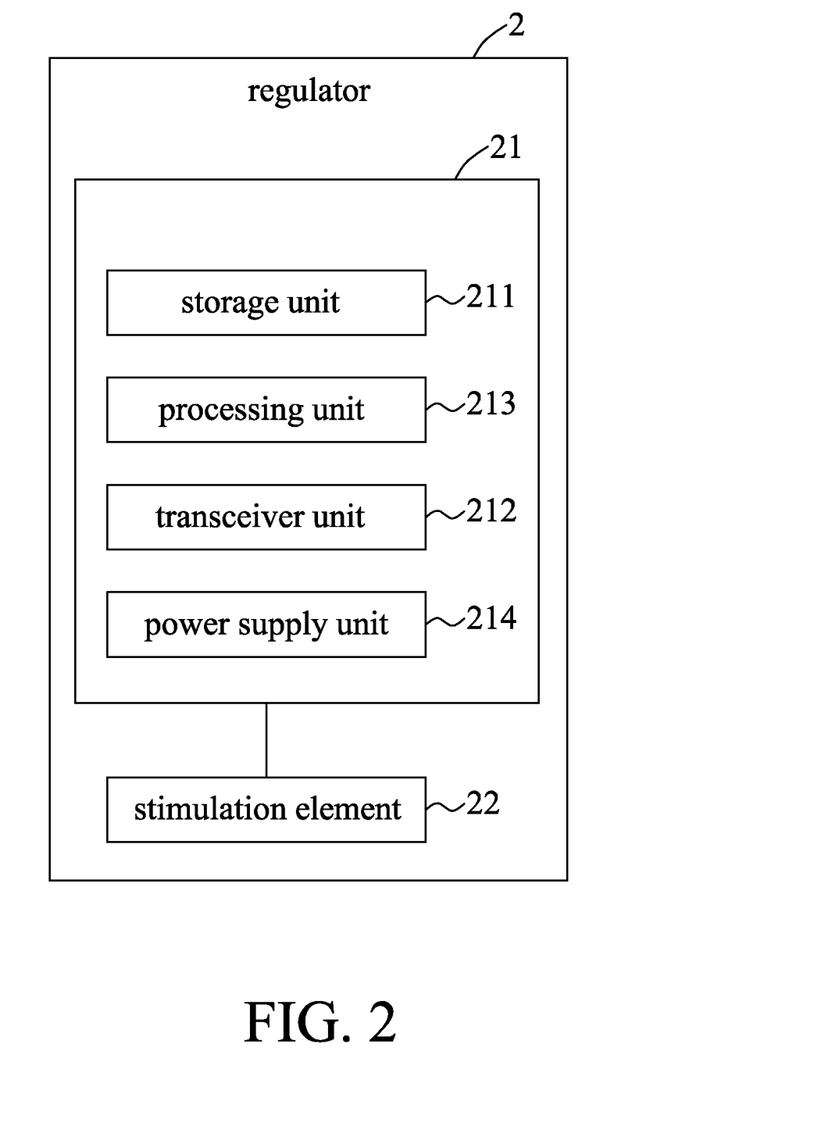
FIG. 2 is a block diagram exemplarily illustrating a regulator of the cardiac pacing device of FIG. 1, according to an embodiment.
Figure 5:
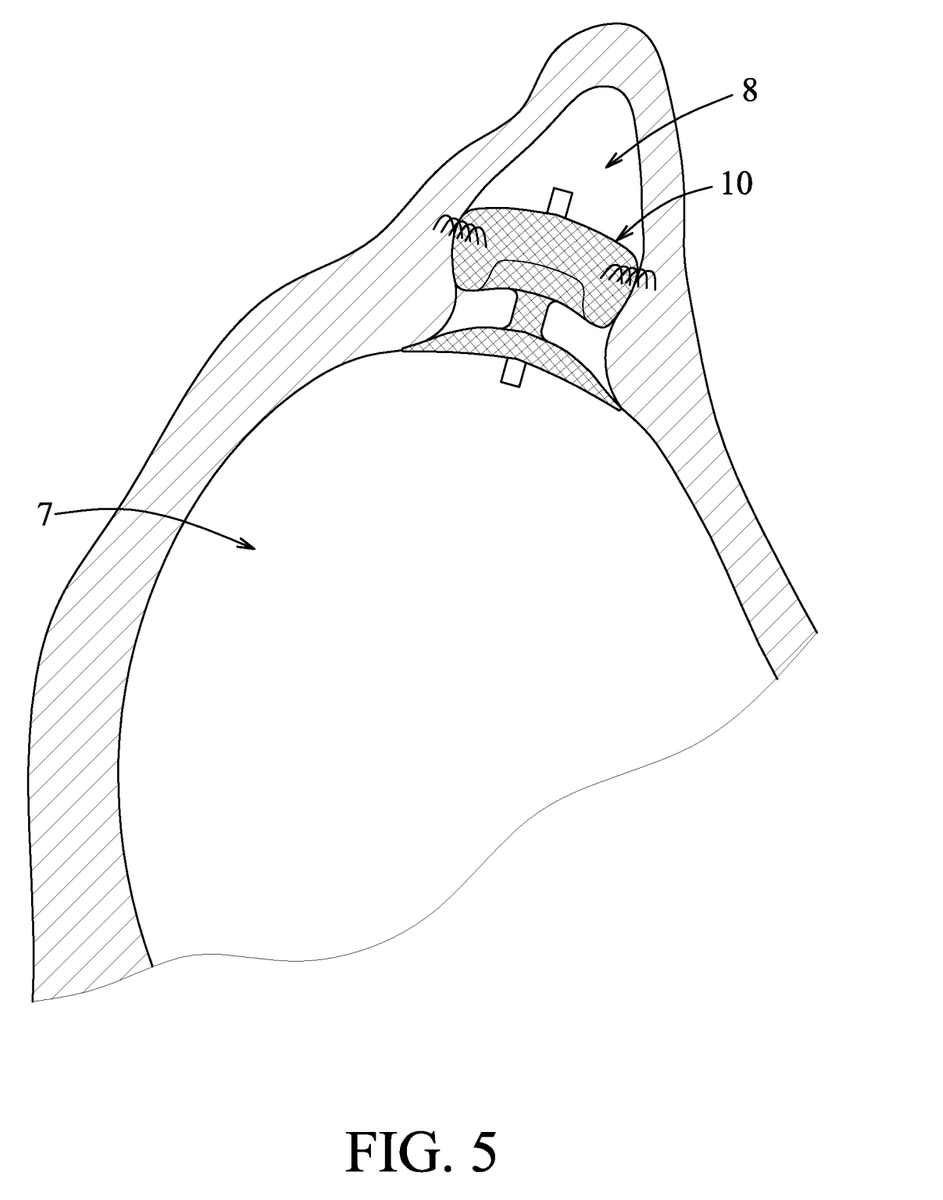
FIG. 5 is a schematic view exemplarily illustrating an example of a cardiac pacing device disposed in a heart between the right atrium and the right atrial appendage, according to an embodiment.

Referring to FIGS. 1, 2 and 5, a first example of a cardiac pacing device 10 is configured to be disposed in a heart between an atrium and an atrial appendage protruding from the atrium. The cardiac pacing device 10 may be disposed between the left atrium 4 and the left atrial appendage 5 protruding from the left atrium 4, as illustrated in FIG. 1, or between the right atrium 7 and the right atrial appendage 8 protruding from the right atrium 7 as illustrated in FIG. 5.

According to an embodiment, the cardiac pacing device 10 includes a blocker 1 and a regulator 2. The blocker 1 is configured to occlude the atrial appendage when the blocker 1 is properly positioned between the atrium and the atrial appendage. In the case of FIG. 1 where the cardiac pacing device 10 is disposed between the left atrium 4 and the left atrial appendage 5, the blocker 1 occludes the left atrial appendage 5; in the case of FIG. 5 where the cardiac pacing device 10 is disposed between the right atrium 7 and the right atrial appendage 8, the blocker 1 occludes the right atrial appendage 8. According to an embodiment, the blocker 1 may be a left atrial appendage occluder (LAA occluder) manufactured by St. Jude Medical Inc. However, the disclosure is not limited thereto, and other available, effective atrial appendage occlusion or closure device may be used. The regulator 2 is attached to the blocker 1, and is configured to contact the heart (e.g., the left atrium 4 in the case of FIG. 1 or the right atrium 7 in the case of FIG. 5) when the blocker 1 is properly positioned between the atrium and the atrial appendage to occlude the atrial appendage, in order to regulate cardiac rhythm of the heart.

According to an embodiment, the blocker 1 includes a first blocking element 11 and a second blocking element 12. The first blocking element 11 is configured to reach into the atrial appendage (e.g., the left atrial appendage 5 in the case of FIG. 1 or the right atrial appendage 8 in the case of FIG. 5) and to occlude the atrial appendage when the blocker 1 is properly positioned between the atrium and the atrial appendage. According to an embodiment, the first blocking element 11 includes a resilient body 111, and a plurality of hooks 112 that are disposed around the resilient body 111 and that are configured for the first blocking element 11 to be caught on an inner wall of the atrial appendage which the first blocking element 11 is to occlude. According to an embodiment, the resilient body 111 may have a self-expandable structure constructed by braided nickel-titanium (nitinol) wires or braided biocompatible polymer wires, and may be covered by a polymer film which may prevent the blood in the atrium from flowing into the atrial appendage so as to prevent a thrombus. The polymer film may be coated with an anticoagulant (e.g., heparin) or other antithrombotic chemical compound in order to be antithrombotic.

According to an embodiment, the second blocking element 12 is configured to close an opening of the atrial appendage, which the blocker 1 is to occlude, where the opening of the atrial appendage communicates with the atrium and defines a boundary between the atrium and the atrial appendage. In an embodiment, the second blocking element 12 includes a disc-shape main body 121 and a connecting element 122 of a certain length that interconnecting a portion of the main body 121 of the second blocking element 12 and a portion of the first blocking element 11 so as to maintain a space between the first blocking element 11 and the main body 121. In an embodiment, at least a portion of the regulator 2 is secured on and along the second blocking element 12 in order for the regulator 2 to be able to contact the atrium (e.g., the left atrium 4 in the case of FIG. 1 or the right atrium 7 in the case of FIG. 5). In an embodiment, a projected area of the main body 121 of the second blocking element 12 on an imaginary plane that is substantially perpendicular to a protruding or extension direction of the atrial appendage is larger than that of the resilient body 111 of the first blocking element 11.

The cardiac pacing device 10 may be disposed into the heart through a catheter. Specifically, in an embodiment, the cardiac pacing device 10 is first guided, through the catheter, to a position in the atrium and close to the opening of the atrial appendage protruding from the atrium. Then, the first blocking element 11 would be forced into the space of the atrial appendage, where the resilient body 111 would expand to occlude the atrial appendage and the hooks 112 would be inserted into the inner wall of the atrial appendage. In this way, the blocker 1 is properly positioned and the first blocking element 11 is firmly fixed in the space of the atrial appendage (with the help of the pressure of the resilient body 111 against the inner wall of the atrial appendage, and the holding force of the hooks 112). At the same time, the main body 121 of the second blocking element 12 closes the opening of the atrial appendage by covering the opening to assist in blocking up most, if not all, of the blood flowing toward the atrial appendage. According to an embodiment, additional hooks (not shown) may be disposed on the main body 121 of the second blocking element 12 (for example, at a surface of the main body 121 that would be close to or near the inner wall of the atrial appendage when the second blocking element 12 is in position) in order to better secure the main body 121 at the opening of the atrial appendage to further ensure occlusion of the atrial appendage.

According to an embodiment, the regulator 2 includes a controlling module 21 and a stimulation element 22 electrically connected to the controlling module 21 (via, for example, the portion of the regulator 2 (e.g., a lead) that is secured on the second blocking element 12), as illustrated in FIG. 2. In an embodiment, the stimulation element 22 is an electrode which is configured to contact the atrium when the cardiac pacing device 10 is in position. According to some embodiments, the stimulation element 22 may be a disc- or umbrella-shaped metal mesh that is secured on the main body 121 of the second blocking element 12 and that covers at least a portion of the outer edge of the main body 121. According to other embodiments, the stimulation element 22 may be a metal chip or rod protruding from the main body 121. The stimulation element 22 is configured to sense a real heart rate of the heart when the cardiac pacing device 10 is in position, and to operate to regulate the cardiac rhythm of the heart by delivering an electrical impulse(s) generated by the controlling module 21 to a muscle(s) of the atrium.

The controlling module 21 is capable of continuously monitoring real-time physiological data (such as heart rate, blood pressure, etc.) of the patient wearing the cardiac pacing device 10, and is configured to regulate the cardiac rhythm when an abnormal condition indicating an abnormal cardiac rhythm of the patient is detected. As illustrated in FIG. 2, the controlling module 21 may include a storage unit 211, a transceiver unit 212, a processing unit 213 electrically connected to the storage unit 211 and the transceiver unit 212, and a power supply unit 214 for supplying electrical power to the storage unit 211, the processing unit 213 and the transceiver unit 212. The power supply unit 214 may be, for example, a battery or a capacitor. The storage unit 211 (e.g., a non-volatile memory) is configured to store a predetermined heart rate corresponding to a normal cardiac rhythm. The processing module 125 is configured to acquire the real heart rate of the heart through the stimulation element 22, to compare the real heart rate thus acquired with the predetermined heart rate stored in the storage module 211, and to regulate the cardiac rhythm of the heart (e.g., by generating an electrical impulse(s) and triggering the stimulation element 22 to stimulate the atrium with the electrical impulse(s) to force the heart to beat in accordance with the predetermined heart rate) based on the comparison result. For example, the processing module 213 may regulate the cardiac rhythm of the heart when a difference between the real heart rate and the predetermined heart rate exceeds a threshold. According to an embodiment, the processing module 213 may be a microcontroller unit (MCU).

The transceiver unit 212 is configured to receive an external instruction that is issued based on an assessment of a doctor and that is from, for example, a smart mobile device or a computer operated by the doctor. The transceiver unit 212 may forward the external instruction to the processing module 213 in order for the processing module 213 to update the predetermined heart rate stored in the storage module 211 based on the content of the external instruction. In an embodiment, the transceiver unit 212 is configured to receive the external instruction via a wireless technology (e.g., Wi-Fi, Bluetooth or ZigBee).

Figure 3:
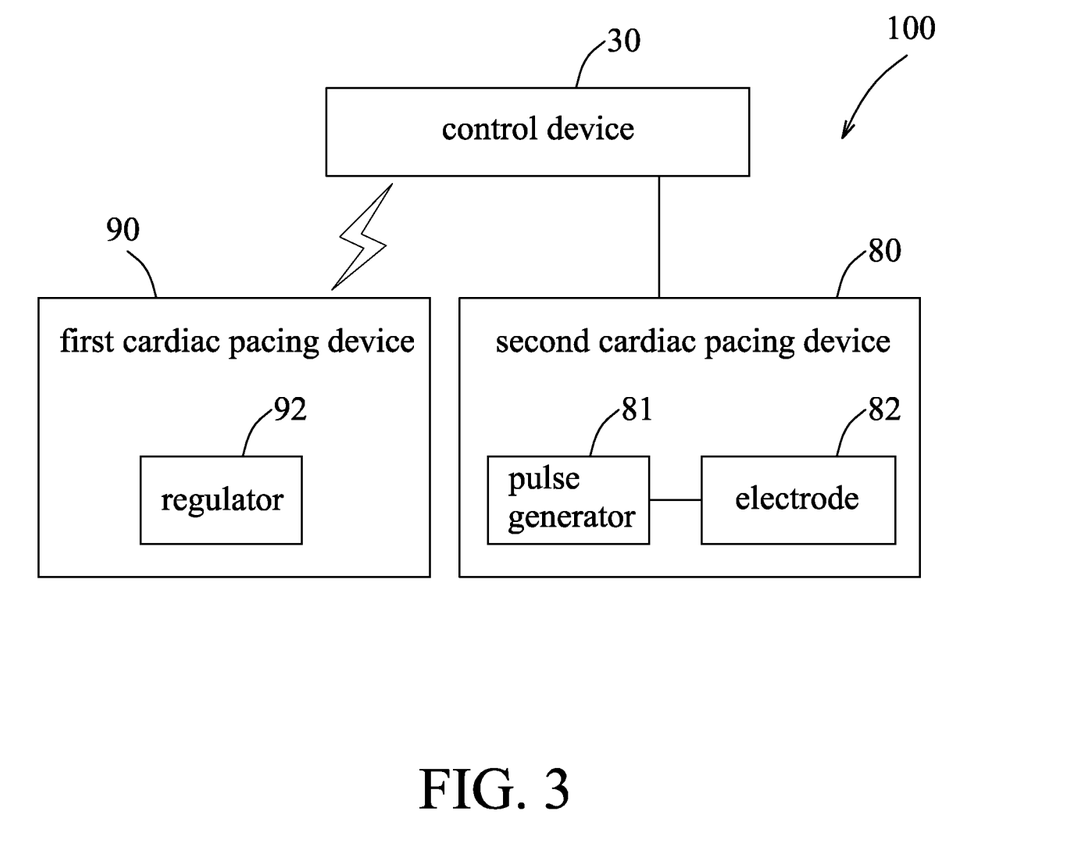
FIG. 3 is a block diagram exemplarily illustrating a cardiac pacing system including first and second cardiac pacing devices and a control device, according to an embodiment.

FIG. 3 is a block diagram which exemplarily illustrates a cardiac pacing system 100 including a first cardiac pacing device 90, a second cardiac pacing device 80, and a control device 30 that is capable of communicating with the first cardiac pacing device 90 and the second cardiac pacing device 80, according to an embodiment of the disclosure. In an embodiment, the first cardiac pacing device 90 is the cardiac pacing device 10 described above.

Figure 4:
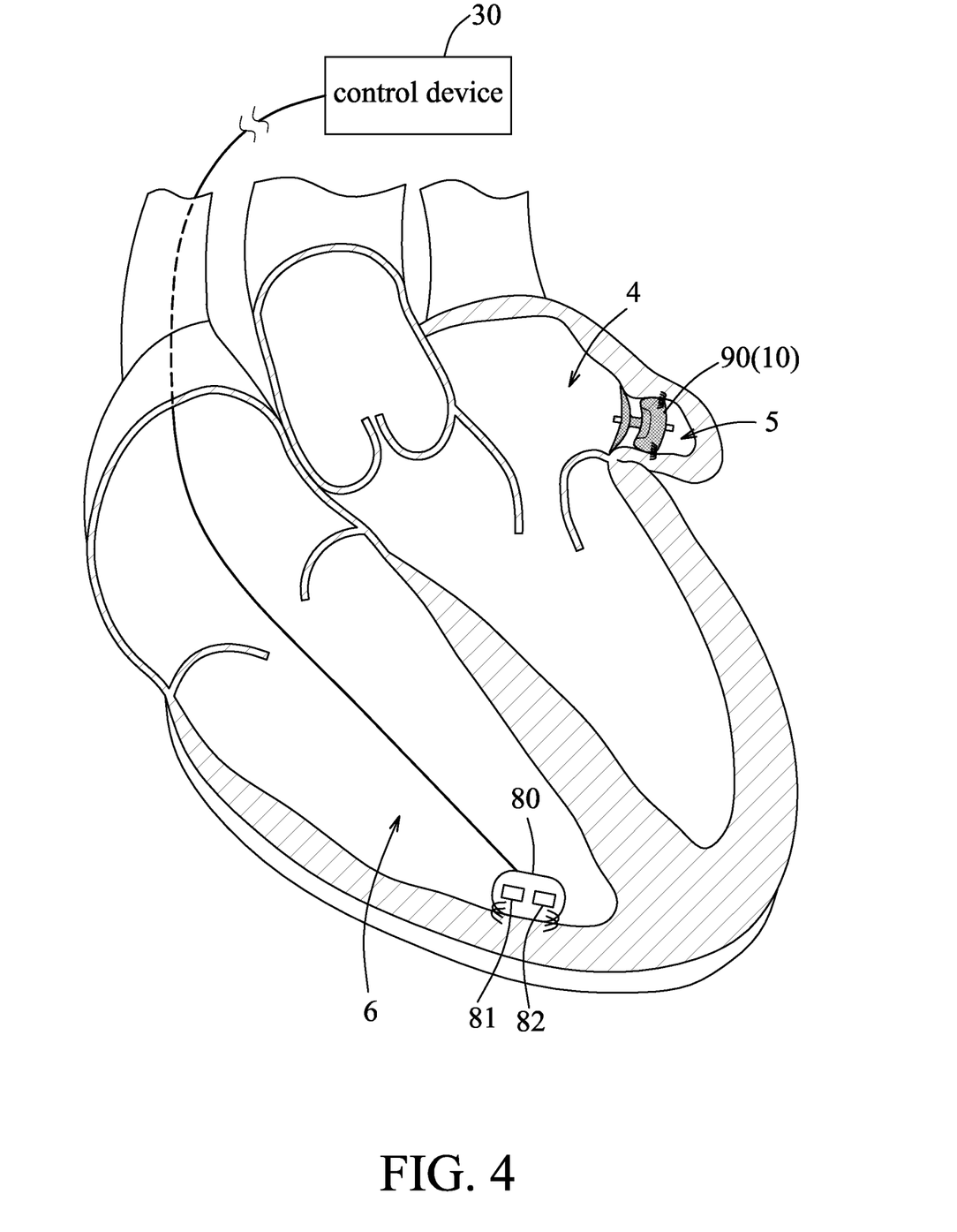
FIG. 4 is a schematic view exemplarily illustrating a configuration of the first and second cardiac pacing devices of the cardiac pacing system implanted in a heart, according to an embodiment.
Figure 6:
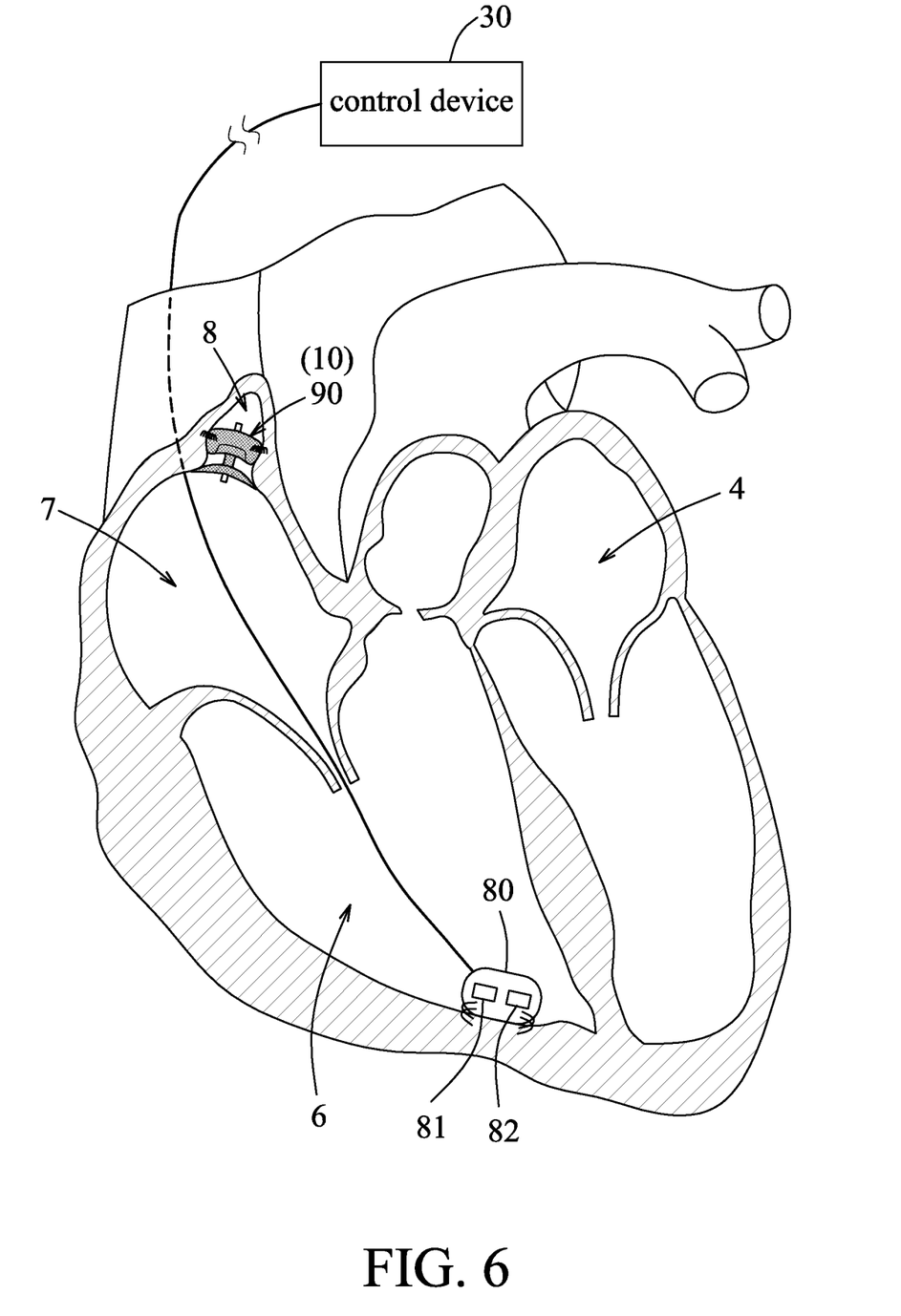
FIG. 6 is a schematic view exemplarily illustrating another configuration of the first and second cardiac pacing devices of the cardiac pacing system implanted in a heart, according to an embodiment.

In an embodiment, each of the first cardiac pacing device 90, the second cardiac pacing device 80 and the control device 30 is an individual, separate device. In particular, the control device 30 is to be disposed inside the body of a patient (e.g., near or under the clavicle of the patient), and the first cardiac pacing device 90 and the second cardiac pacing device 80 are to be disposed separately inside the heart of the patient, as illustrated in FIGS. 4 and 6 (where the first cardiac pacing device 90 is illustrated as the cardiac pacing device 10). In another embodiment, the control device 30 is combined or incorporated with one of the first cardiac pacing device 90 and the second cardiac pacing device 80, and is to be disposed in the heart along with said one of the first cardiac pacing device 90 and the second cardiac pacing device 80.

According to an embodiment, the first cardiac pacing device 90 includes a regulator 92 in which a first predetermined heart rate is stored, and is to be disposed in the heart between an atrium and an atrial appendage protruding from the atrium. In a case that the first cardiac pacing device 90 is the cardiac pacing device 10, the regulator 92 of the first cardiac pacing device 90 refers to the regulator 2 of the cardiac pacing device 10. Specifically, the first cardiac pacing device 90 may be disposed between the left atrium 4 and the left atrial appendage 5 protruding from the left atrium 4, as illustrated in FIG. 4, or between the right atrium 7 and the right atrial appendage 8 protruding from the right atrium 7 as illustrated in FIG. 6.

According to an embodiment, the second cardiac pacing device 80 includes a pulse generator 81 and an electrode 82 electrically connected with the pulse generator 81, and is to be disposed in the right ventricle 6 of the heart, as illustrated in FIGS. 4 and 6. The electrode 82 is configured to touch the right ventricle 6 when the second cardiac pacing device 80 is in place. The pulse generator 81 stores, in its storage (not shown), a second predetermined heart rate (which may relate to a frequency or a period of a wave representative of the cardiac rhythm), and is configured to sense the heart rate of the heart through the electrode 82, and to output, when needed, an electrical impulse(s) to be transmitted via the electrode 82 to the right ventricle 6 to stimulate the muscle(s) of the right ventricle 6 in order to regulate the cardiac rhythm of the right ventricle 6. The operation of the second cardiac pacing device 80 may resemble a VVI pacemaker, and the second cardiac pacing device 80 is configured to pace or regulate the cardiac rhythm of the right ventricle according to the second predetermined heart rate stored therein. Any available, effective artificial pacemaker may be used as the second cardiac pacing device 80.

According to an embodiment, the control device 30 is configured to control and coordinate the first cardiac pacing device 90 and the second cardiac pacing device 80, and may trigger at least one of the first cardiac pacing device 90 or the second cardiac pacing device 80 to stimulate at least one of the left/right atrium or the right ventricle in order to regulate the cardiac rhythm of at least one of the left/right atrium or the right ventricle. According to an embodiment, the control device 30 is capable of communicating with the first cardiac pacing device 90 (especially the regulator 92) via a wireless technology (e.g., Wi-Fi, Bluetooth or ZigBee), and communicating with the second cardiac pacing device 80 (especially the pulse generator 81) via a wire (e.g., a lead) or a wireless technology (e.g., Wi-Fi, Bluetooth or ZigBee). In the case that the first cardiac pacing device 90 is the cardiac pacing device 10, the communication between the control device 30 and the cardiac pacing device 10 may be through the transceiver unit 212. In a case that the control device 30 is incorporated in one of the first cardiac pacing device 90 and the second cardiac pacing device 80, the first and second cardiac pacing devices 90, 80 may be configured to be able to communicate with each other via a wireless technology (e.g., Wi-Fi, Bluetooth or ZigBee) in order to be able to cooperate with each other to conduct a cardiac regulation operation.

In an embodiment, the control device 30 may control and/or coordinate the first cardiac pacing device 90 (which manages sensing and pacing of the left or right atrium, depending on where the first cardiac pacing device 90 is installed) and the second cardiac pacing device 20 (which manages sensing and pacing of the right ventricle) for the cardiac pacing system 100 to function as a DDD pacemaker that may pace both of the left (or right) atrium and the right ventricle simultaneously as needed. The cardiac pacing system 100 may also function as a VDD pacemaker. For example, when the cardiac rhythm of the right ventricle becomes slower than a predetermined heart rate (i.e., the second predetermined heart rate stored in the second cardiac pacing device 80) such that conducting function of the right ventricle fails, the control device 30 may trigger the second cardiac pacing device 80 to pace the right ventricle (i.e., send an electrical impulse(s) to the right ventricle) based on the P-wave sensed by the second cardiac pacing device 80. The cardiac pacing system 100 may also function as an AAI pacemaker. For example, when the control device 30 detects an overly-slow cardiac frequency of the left/right atrium and good atrioventricular (AV) conduction based on information from the first cardiac pacing device 90 (e.g., from the processing unit 213 of the cardiac pacing device 10), the control device 30 may trigger the first cardiac pacing device 90 to pace the left/right atrium in accordance with the first predetermined heart rate stored in the regulator 92. Then, the electrical impulse would be transmitted to the right ventricle for the right ventricle to be paced in accordance with the first predetermined heart rate, such that the atrium and the ventricle may keep contracting in a continuous and synchronized way.

Figure 7:
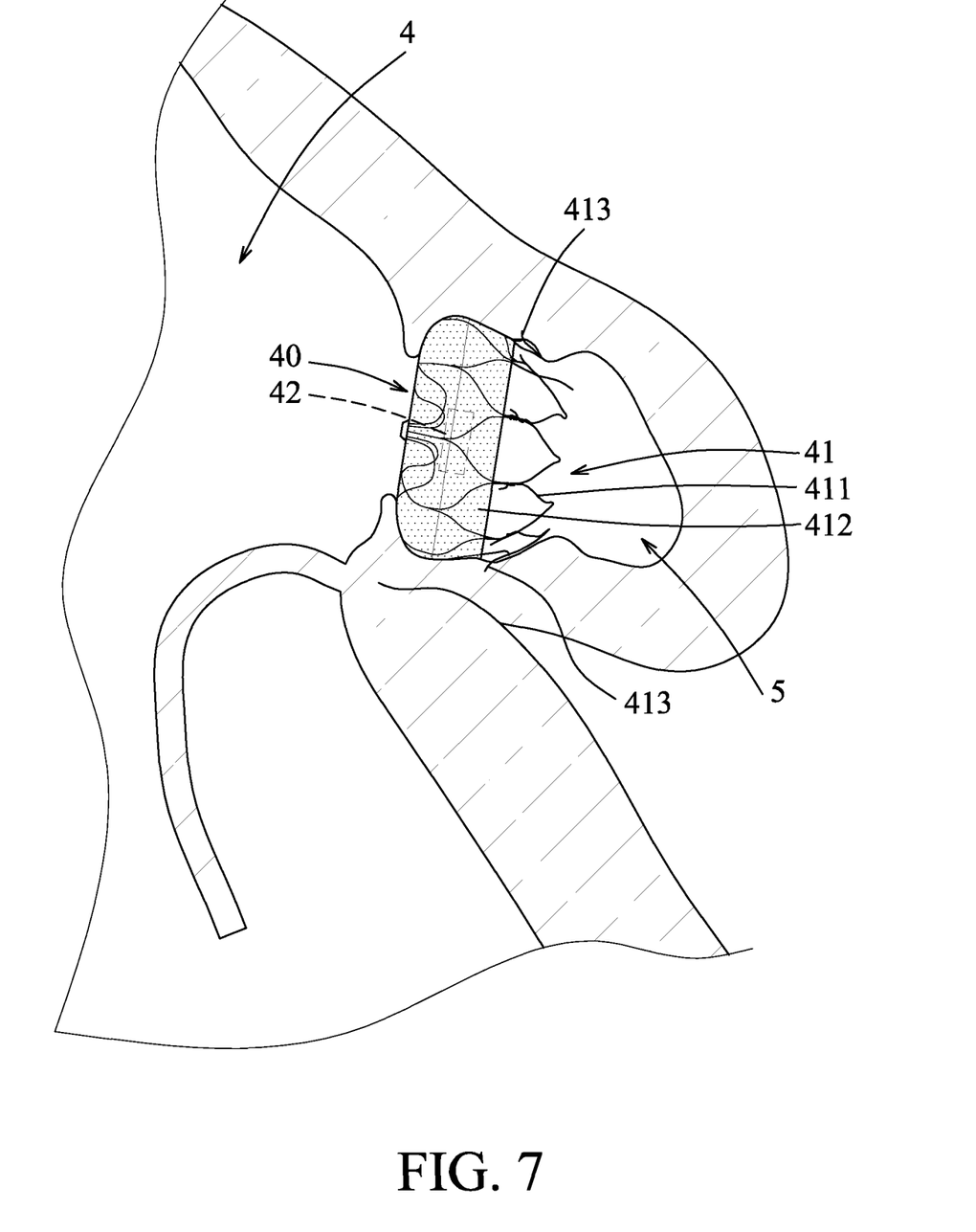
FIG. 7 is a schematic view exemplarily illustrating another example of a cardiac pacing device disposed in a heart between the left atrium and the left atrial appendage, according to an embodiment.
Figure 8:
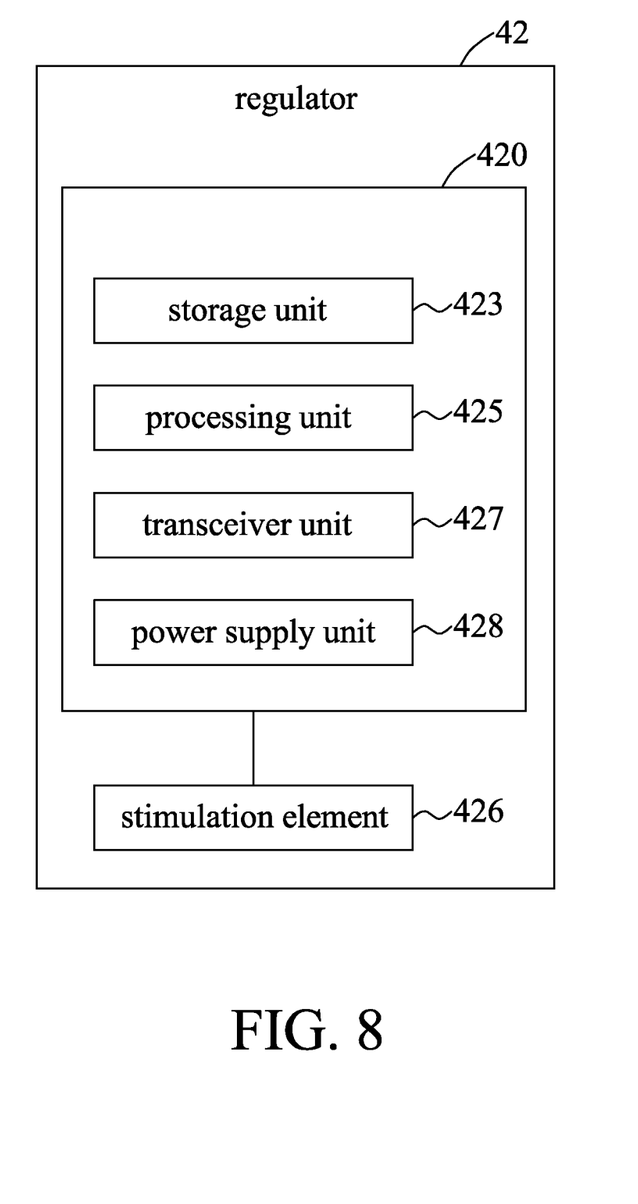
FIG. 8 is a block diagram exemplarily illustrating a regulator of the cardiac pacing device of FIG. 7, according to an embodiment.
Figure 9:
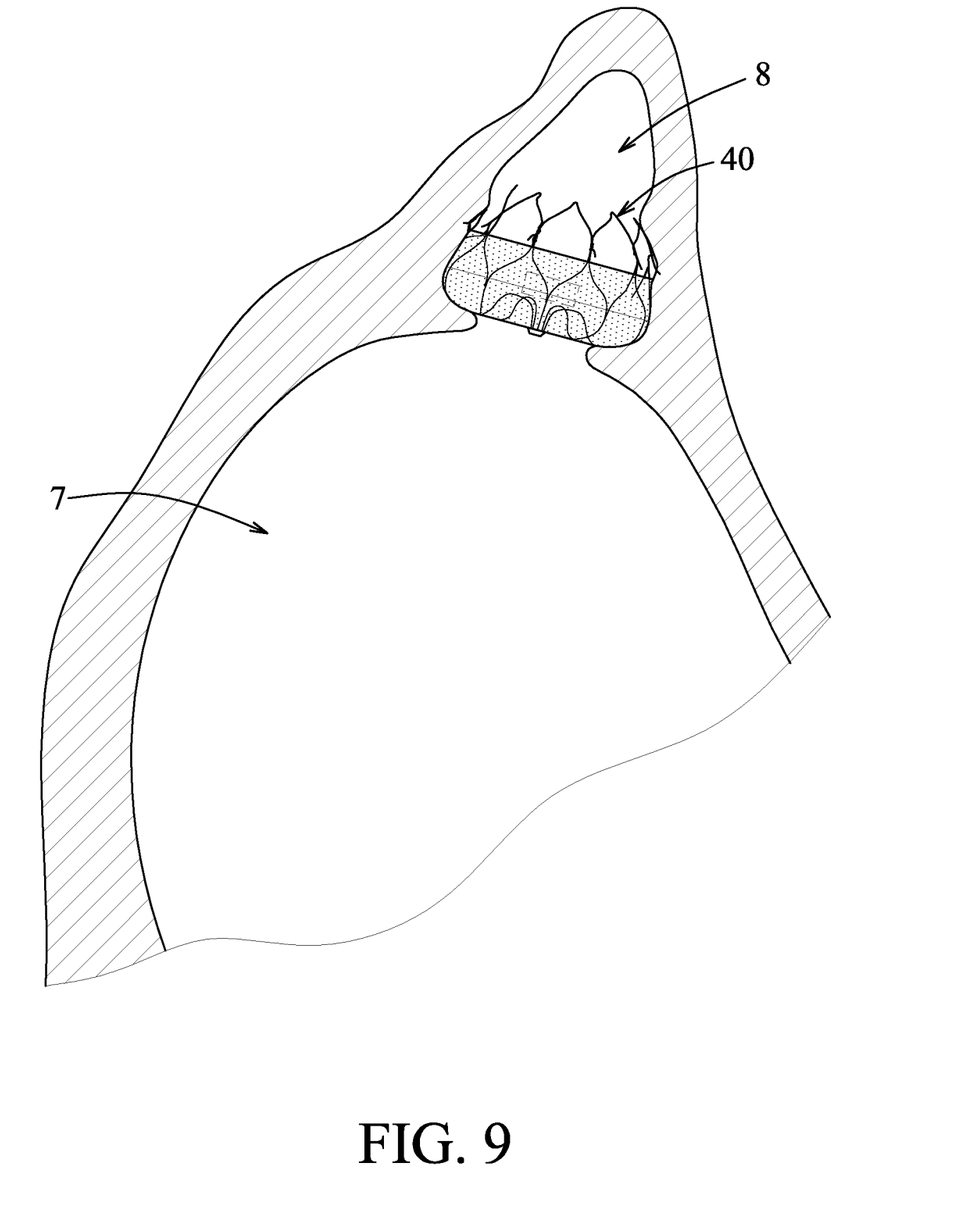
FIG. 9 is a schematic view exemplarily illustrating an example of a cardiac pacing device disposed in a heart between the right atrium and the right atrial appendage, according to an embodiment.

Referring to FIGS. 7-9, another example of a cardiac pacing device 40 that is to be disposed in a heart between an atrium and an atrial appendage protruding from the atrium is disclosed. The cardiac pacing device 40 may be disposed between the left atrium 4 and the left atrial appendage 5 protruding from the left atrium 4, as illustrated in FIG. 7, or between the right atrium 7 and the right atrial appendage 8 protruding from the right atrium 7 as illustrated in FIG. 9. Just like the cardiac pacing device 10, the cardiac pacing device 40 may be used as the cardiac pacing device 90 of the cardiac pacing system 100 of FIG. 3.

According to an embodiment, the cardiac pacing device 40 includes a blocker 41 and a regulator 42. The blocker 41 is configured to occlude the atrial appendage when the blocker 41 is properly positioned between the atrium and the atrial appendage. In the case of FIG. 7 where the cardiac pacing device 40 is disposed between the left atrium 4 and the left atrial appendage 5, the blocker 41 occludes the left atrial appendage 5; in the case of FIG. 9 where the cardiac pacing device 40 is disposed between the right atrium 7 and the right atrial appendage 8, the blocker 41 occludes the right atrial appendage 8. According to an embodiment, the blocker 41 may be a left atrial appendage closure device manufactured by Boston Scientific Corporation. However, the disclosure is not limited thereto, and other available, effective atrial appendage occlusion or closure device may be used as well. The regulator 42 is attached to the blocker 41, and is configured to contact the heart (e.g., the left atrium 4 in the case of FIG. 7 or the right atrium 7 in the case of FIG. 9) when the blocker 41 is properly positioned between the atrium and the atrial appendage and occludes the atrial appendage, in order to regulate cardiac rhythm of the heart.

According to an embodiment, the blocker 41 includes a self-expandable metallic stent (SEMS) 411 and a mesh screen 412. According to an embodiment, the SEMS 411 may have a self-expandable structure constructed by nickel-titanium alloy, and is configured to be jammed into an opening of the atrial appendage that communicates with the atrium and defines a boundary between the atrium and the atrial appendage when the blocker 41 is properly positioned between the atrium and the atrial appendage. The SEMS 411 may include a plurality of barbs 413 that are disposed around a periphery of the SEMS 411 and that are configured for the SEMS 411 to be caught on an inner wall of the atrial appendage (e.g., the left atrial appendage 5 in FIG. 7). The mesh screen 412 may be, for example, a porous and expandable osmotic membrane made of polytetrafluoroethylene (PTFE). The mesh screen 412 covers a portion of an outer surface of the SEMS 411, such that the mesh screen 412 cooperates with the SEMS 411 to close the opening when the blocker 41 is in position, in order to prevent a clot that is formed by stagnating blood in the atrial appendage.

According to an embodiment, the regulator 42 includes a controlling module 420 and a stimulation element 426 electrically connected to the controlling module 420, wherein the controlling module 420 includes a storage unit 423, a transceiver unit 427, a processing unit 425 electrically connected to the storage unit 423 and the transceiver unit 427, and a power supply unit 428 for supplying electrical power to the storage unit 423, the processing unit 425, and the transceiver unit 427, as illustrated in FIG. 8. As can be seen from FIGS. 2 and 8, the structure of the regulator 42 of the cardiac pacing device 40 resembles the regulator 2 of the cardiac pacing device 10 described above. Therefore, characteristics of the regulator 42 (and the elements thereof) that are similar to the regulator 2 (and the elements thereof) are not repeated here, and the following description only focuses on characteristics of the regulator 42 that are different from those of the regulator 2.

In an embodiment, the controlling module 420 is positioned inside the SEMS 411, and the stimulation element 426 is a lead that extends, from the controlling module 420, out of the SEMS 411 to contact the atrial appendage when the blocker 41 is in position, such that the regulator 42 may deliver an electrical impulse(s) through the stimulation element 426 to the atrial appendage to force the heart to beat in accordance with the predetermined heart rate stored in the storage unit 423.

A favorable characteristic of the disclosed cardiac pacing device 10, 40 that is configured to be disposed between an atrium and an auricular appendage protruding from the atrium is reduction of the foreign body sensation that may be caused by conventional pacemakers disposed in ventricles, while beneficially closing an opening of the atrial appendage that communicates with the atrium and defines the boundary between the atrium and the auricular appendage to prevent blood flow from the atrium to the atrial appendage.

A favorable characteristic of the disclosed cardiac pacing system 100 is that the control device 30 may trigger at least one of the first cardiac pacing device 90 or the second cardiac pacing device 80 to pace the atrium and/or the atrial appendage according to an actual demand. Therefore, a treatment to bradycardia, continuous biventricular pacing or atrial fibrillation that may depend on the sensed heart rate(s) of single or dual chamber can be accomplished by the disclosed cardiac pacing system 100.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A cardiac pacing device to be disposed in a heart between an atrium and an atrial appendage protruding from the atrium, the atrial appendage having an opening that communicates with the atrium and that defines a boundary between the atrium and the atrial appendage, said cardiac pacing device comprising:
    a blocker configured to occlude the atrial appendage, and including:
        a first blocking element configured to reach into the atrial appendage and to occlude the atrial appendage when said blocker is positioned, and
        a second blocking element connected with said first blocking element, and configured to close the opening of the atrial appendage when said blocker is positioned; and
    a regulator having a portion that is secured on said second blocking element, and configured to contact the atrium when said blocker is positioned between the atrium and the atrial appendage to occlude the atrial appendage in order to regulate cardiac rhythm of the heart;
    wherein said regulator includes:
        a storage unit configured to store a predetermined heart rate corresponding to a normal cardiac rhythm;
        a stimulation element configured to, when said blocker is positioned, contact the atrium and sense a real heart rate of the heart; and
        a processing unit electrically connected to said storage unit and said stimulation element, said processing unit being configured to acquire the real heart rate of the heart through said stimulation element, to compare the real heart rate thus acquired with the predetermined heart rate stored in said storage unit, and to trigger, when determining that a difference between the real heart rate and the predetermined heart rate exceeds a threshold, said stimulation element to stimulate the atrium to force the heart to beat in accordance with the predetermined heart rate.

2. The cardiac pacing device of claim 1, wherein said first blocking element includes a body, and a plurality of hooks that are disposed around said body and that are configured for said first blocking element to be caught on an inner wall of the atrial appendage when said blocker is positioned.

3. The cardiac pacing device of claim 1, wherein said regulator further includes:
    a transceiver unit electrically connected to said storage unit, and configured to receive an external instruction for the predetermined heart rate stored in said storage unit to be updated based on the external instruction.

4. The cardiac pacing device of claim 1, wherein said regulator further includes a power supply unit for providing electrical power to said storage unit and said processing unit.

5. The cardiac pacing device of claim 1, wherein said cardiac pacing device is to be disposed between a left atrium and a left atrial appendage of the heart.

6. The cardiac pacing device of claim 1, wherein said cardiac pacing device is to be disposed between a right atrium and a right atrial appendage of the heart.

7. A cardiac pacing device to be disposed in a heart between an atrium and an atrial appendage protruding from the atrium, the atrial appendage having an opening that communicates with the atrium and that defines a boundary between the atrium and the atrial appendage, said cardiac pacing device comprising:
    a blocker configured to occlude the atrial appendage, and including:
        a self-expandable metallic stent (SEMS) configured to be jammed into the opening of the atrial appendage when said blocker is positioned, said SEMS including a plurality of barbs that are disposed around a periphery of said SEMS and that are configured for said SEMS to be caught on an inner wall of the atrial appendage, and
        a mesh screen covering a portion of an outer surface of said SEMS; and
    a regulator attached to said blocker, and including:
        a stimulation element which is to contact the atrial appendage and sense a real heart rate of the heart when said blocker is positioned between the atrium and the atrial appendage to occlude the atrial appendage in order to regulate cardiac rhythm of the heart; and
        a controlling module which is positioned inside said SEMS and which is electrically connected to said stimulation element, said controlling module including:
            a storage unit configured to store a predetermined heart rate corresponding to a normal cardiac rhythm; and
            a processing unit electrically connected to said storage unit and said stimulation element, said processing unit being configured to acquire the real heart rate of the heart through said stimulation element, to compare the real heart rate thus acquired with the predetermined heart rate stored in said storage unit, and to trigger, when determining that a difference between the real heart rate and the predetermined heart rate exceeds a threshold, said stimulation element to stimulate the atrial appendage to force the heart to beat in accordance with the predetermined heart rate.

8. The cardiac pacing device of claim 7, wherein said regulator further includes:
    a transceiver unit electrically connected to said storage unit, and configured to receive an external instruction for the predetermined heart rate stored in said storage unit to be updated based on the external instruction.

* * * * *